United States Patent [19]
Dutcher et al.

[11] 4,350,169
[45] Sep. 21, 1982

[54] FLEXIBLE TIP STIFFENING STYLET FOR USE WITH BODY IMPLANTABLE LEAD

[75] Inventors: Robert G. Dutcher, Columbia Heights; James E. Upton, New Brighton, both of Minn.

[73] Assignee: Medtronic, Inc., Minneapolis, Minn.

[21] Appl. No.: 176,410

[22] Filed: Aug. 8, 1980

Related U.S. Application Data

[63] Continuation of Ser. No. 1,203, Jan. 5, 1979, abandoned.

[51] Int. Cl.³ .............................................. H61N 1/00
[52] U.S. Cl. .................................... 128/783; 128/419
[58] Field of Search ................ 128/783, 784, 786, 419

[56] References Cited

U.S. PATENT DOCUMENTS 3,995,623 12/1976 Blake et al. ...................... 128/419 P

FOREIGN PATENT DOCUMENTS 2539553 3/1977 Fed. Rep. of Germany ...... 128/785
2119261 7/1972 France .

Primary Examiner—William E. Kamm
Attorney, Agent, or Firm—Schroeder, Siegfried, Vidas, Steffey & Arrett

[57] ABSTRACT

A body implantable lead and a stiffening stylet with a flexible tip for imparting rigidity to the lead to facilitate attachment of the lead to an internal body organ and for transmitting torque to the distal end of the lead. A flexible tip stiffening stylet is provided for insertion into a lumen in the lead extending from a pin at its proximal end along the length of the lead conductor to the electrode. A portion of the stylet wire inserted in the lumen has a thinner diameter over a portion of its length near the distal end to permit smooth transmission of torque by rotation of the stylet wire even in applications where the lead and stylet are tightly bent in the vicinity of the thinned portion of the lead.

11 Claims, 4 Drawing Figures

U.S. Patent  Sep. 21, 1982  4,350,169
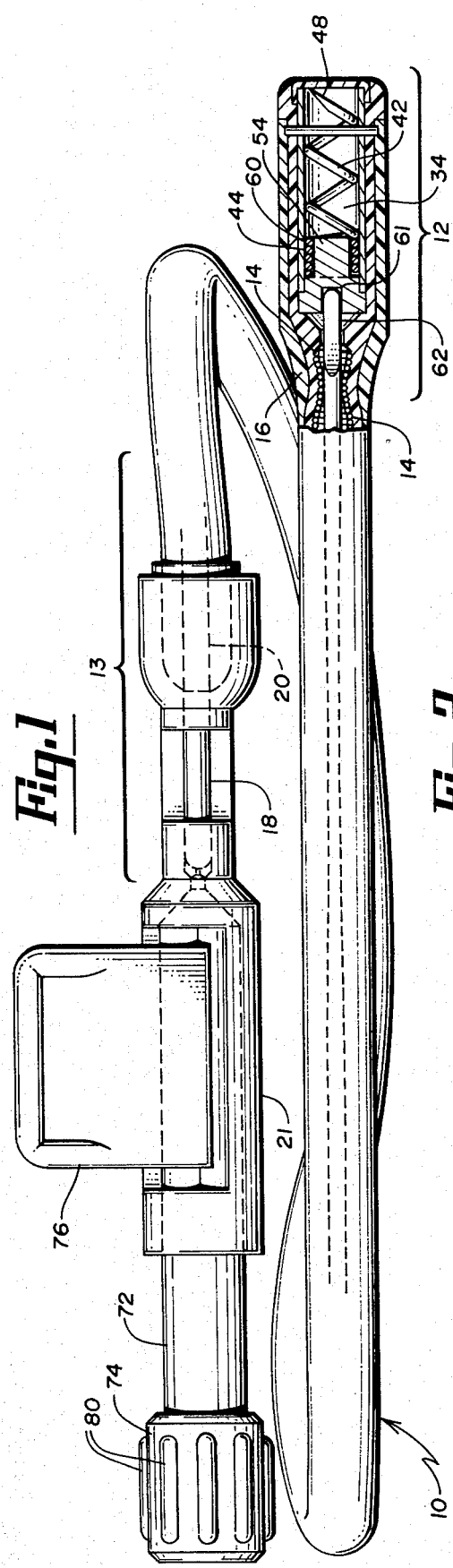
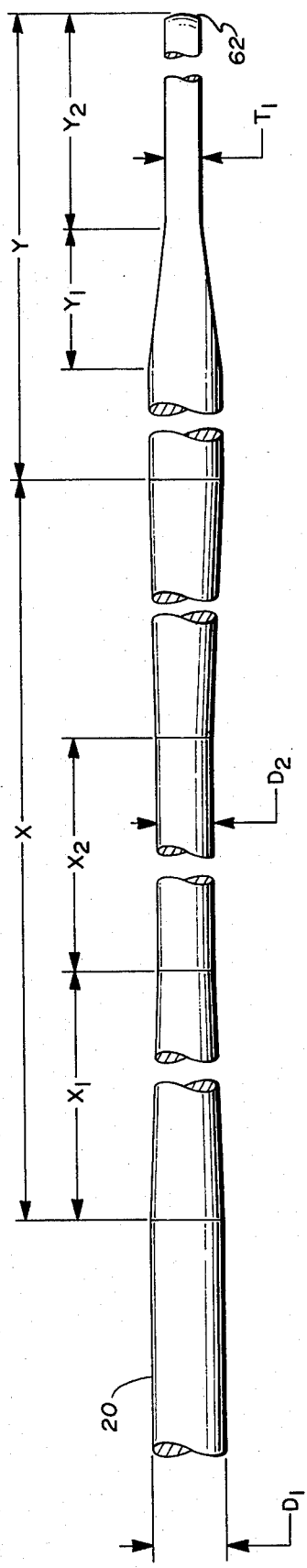
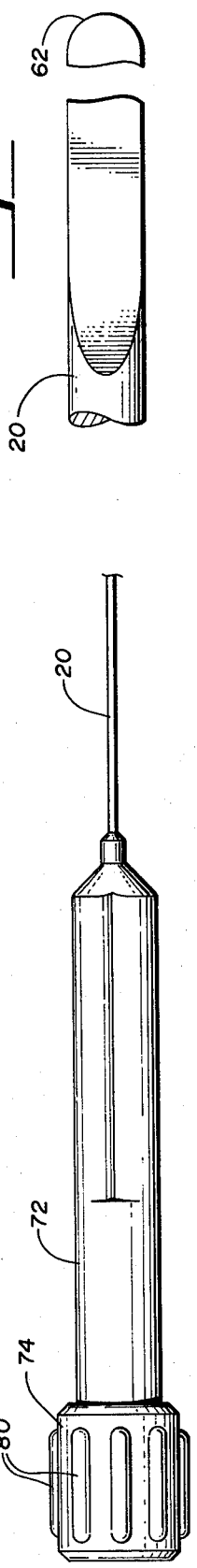
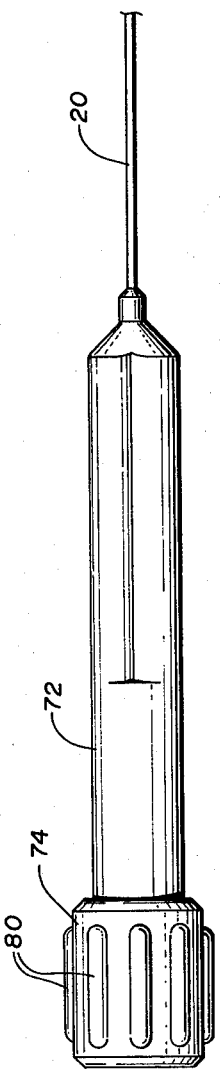

FLEXIBLE TIP STIFFENING STYLET FOR USE WITH BODY IMPLANTABLE LEAD

This is a continuation of application Ser. No. 001,203 filed Jan. 5, 1979, now abandoned.

DESCRIPTION

BACKGROUND OF THE INVENTION

This invention relates to a stylet for use with a lead bearing an electrode for electrically connecting an organ inside a living animal body to an electrical device. Notwithstanding its various uses, this invention will be described for use as an endocardial pacing and sensing lead for connecting an artificial cardiac pacemaker to cardiac tissue.

Endocardial pacing and sensing leads of the type shown in U.S. patent application Ser. No. 839,062, filed Oct. 3, 1977, now U.S. Pat. No. 4,217,913 for a Body Implantable Lead With Protected Extendable Tissue Securing Means, for example, comprise one or more lengths of hollow, coiled wire conductor encased within a suitable insulating material, such as silicone rubber, that is substantially inert to body fluids and tissues, a hollow connector pin attached to the proximal end of each of the conductors, and an electrically conductive electrode at the distal end of each of the conductors adapted to be placed in contact with the endocardium of the patient. A lumen extends through each pin and the corresponding lengths of coiled wire conductor to the electrode at the distal ends thereof and receives a stiffening stylet of cylindrical corrosion resistant wire for imparting stiffness to the lead to facilitate its advancement through the venous system of the patient and into the apex of the right ventricle. With the stylet removed from the lead, the lead is very flexible and difficult to so advance. Further details of the construction and utility of such endocardial pacing leads may be obtained by reference to U.S. Pat. Nos. 3,348,584 and 4,046,151, as well as the above-identified pending application Ser. No. 839,062.

An improved cardiac pacing lead employing a rigid helix with a sharp tipped distal end adapted to be screwed into the endocardium is disclosed in co-pending U.S. patent application Ser. No. 839,062, which is assigned to Medtronic, Inc. The improved lead disclosed in that application can be lodged in and permanently secured to or removed from body tissue without the use of bulky sleeves or catheter introducers to protect the patient's veins and tricuspid valve from snagging on the sharp tip of the helix.

In the improved lead disclosed in Ser. No. 839,062, the tissue securing means is a helix with a piston member fixed to its proximal end and positioned in a chamber within the electrode body. A stylet having a knob at its proximal end is passed through a lumen in the lead which communicates with the opening in the proximal end of the lead body such that the distal end of the stylet which is shaped in the form of a screwdriver head, is engagable with a slot in the head of the piston means. The stylet may be rotated after the distal end of the lead is positioned near the endocardial tissue and when the stylet is rotated the piston means is caused to screw the helix out of the distal opening in the electrode lead and into the endocardial and myocardial tissue to secure the electrode.

The implantable lead of the present invention incorporates an improved stylet to increase the effectiveness in the placement of either the endocardial leads of the type disclosed in U.S. Pat. No. 4,046,151, or in the co-pending application Ser. No. 839,062. A feature of the present invention is the provision of a stylet adapted to be extremely flexible in the vicinity of the distal end of the lead to increase the flexibility of the lead without detracting from the ability of the lead to transmit torque from its proximal end to its distal end. The improved structure facilitates the transmission of torque by the stylet even when the stylet and lead are sharply bent. The improved structure also permits the stylet and lead to be used where it is necessary to pass them through a sharp bend during insertion. Additionally, the improved flexible stylet may be inserted with less chance of snagging the helical coil conductor of the lead and perforating either the lead or surrounding tissue. The improved structure also provides an improved screwdriver tip for inserting the electrode into the tissue into which it is to be lodged.

SUMMARY OF THE INVENTION

The above features and advantages of the present invention, as well as others, are accomplished by providing a body implantable lead of the type having a lumen for receiving a stiffening stylet extending through the connector pin of the lead at its proximal end, through the length of the lead and to the electrode at the distal end thereof with an improved stiffening stylet having a flexible tip having sufficient flexibility to permit the stylet to follow the path of a lumen having a relatively severe bend therein as would be the case when the lead is lodged in the right atrium rather than the right ventricle. The improved stiffening stylet comprises a length of stylet wire having a portion of reduced diameter in the vicinity of the distal end thereof and an improved screwdriver tip.

Other features, advantages, and objects of the present invention will hereinafter become more fully apparent from the following description of the drawings, which illustrate the invention.

BRIEF DESCRIPTION OF THE DRAWINGS

FIG. 1 is a view of a preferred embodiment of the body implantable lead of the present invention showing in phantom outline form the thinned portion of the stylet;

FIG. 2 is an enlarged side view of the distal end of the stylet of FIG. 1 showing the variations in diameter according to the present invention; and FIG. 3 is an enlarged top view of the extreme distal end portion of the stylet; and FIG. 4 is an enlarged view of the extreme proximal end portion of the stylet.

DESCRIPTION OF THE PREFERRED EMBODIMENT

Referring now to the preferred embodiment of the invention depicted in FIG. 1, there is shown in intravascular endocardial lead comprising an elongated lead 10, a distal electrode end portion 12, and a proximal terminal end portion 13. The lead, in unipolar configuration, comprises a closely wound, coiled conductor 14 in the form of a spring spirally wound about and along the axis of the conductor. The spring coil 14 extends through the length of lead 10 in a lumen of a jacket or sleeve 16 of electrically insulating material.

The structure and operation of the distal end portion 12 of lead 10 are discussed in detail in co-pending application Ser. No. 839,062 and the reference characters used in that application have been carried over to the present application where appropriate. As more fully described in that application, a tissue securing member in the form of a rlatively rigid circular corkscrew or helix 42 is provided having a proximal end 44 of several closely wound turns located in the chamber 34 toward the proximal end thereof. Helix 42 has a sharpened tip 48.

The stylet used in the preferred embodiment of the invention disclosed herein is shown in detail in FIGS. 2 and 3. The stylet is made of a corrosion resistant steel, such as type 304 stainless steel wire, having a typical nominal diameter over most of its length of approximately 0.016 inches. This dimension is represented on FIG. 2 as D1, and corresponds to the diameter of prior art stylets conventionally used in positioning leads of the type generally shown in FIG. 1. As shown in FIG. 2, the preferred embodiment of the stylet disclosed herein has a reduced diameter portion near the distal end to facilitate transmission of rotational torque by the stylet in situations where the stylet and lead assembly are sharply bent in the vicinity of the distal end of the lead.

Attempts to achieve adequate transmission of rotational torque through a sharply bent stylet have included providing cylindrical stylets having uniform reduced diameters over their entire length. Those attempts have been unsuccessful since the reduction of the diameter of the entire stylet tends to weaken it unnecessarily and to make transmission of significant rotational torque difficult. In the stylet shown in FIG. 2, the reduced diameter portion is provided only in the area which is subject to the extreme bending. This extreme bending can be expected, for example, in cases where the lead 10 is implanted in the right atrium of the heart, rather than the apex of the right ventricle. Another situation where the stylet is of utility is in a ventricular implantation where the tricuspid valve between the right atrium and right ventricle places a relatively sharp bend in the lead. In both situations, the reduced diameter portions of the lead are located only in the vicinity of the bend. In such situations, the improved stylet can be inserted into the lead with a lessened risk of snagging at the bend and consequent damage to the lead and surrounding tissue. After insertion of the stylet, its improved structure provides for adequate transmission of rotational torque to permit implantation.

In the preferred embodiment of the improved stylet for use with a cardiac pacing lead 10, the length of the stylet from its screwdriver tip porton 62 to the proximal end of the stylet is slightly over 26 inches. As shown in FIG. 2, the reduced diameter portion is provided near the distal end. Typical dimensions for distances X and Y are four inches and one-half inch respectively. The smooth transition between the diameter D1 and the diameter D2 is indicated by the dimension X1, which may typically be in the range of three quarters of an inch, while the actual reduced diameter portion, indicated by D2, may typically be approximately two and one-half inches long, with a diameter of 0.013 inches. The distal end of the stylet is formed into a screwdriver tip 62, having a length Y2 of typically 0.15 inches and a tapered length Y1 of 0.03 inches typically. As shown in FIG. 3, the tip 62 has a radius of 0.008 inches and a thickness T1 is viewed in FIG. 2 of 0.008 inches.

In some applications, it may be necessary to utilize a standard uniform diameter stylet to stiffen the lead to facilitate insertion of the lead through the venous system and into the chamber of the heart where the helix 42 is desired to be implanted. After the lead is inserted and positioned, the insertion stylet is removed and the flexible tip stylet may then be inserted and utilized for the remainder of the implanting process. The flexible tip portion of the stylet makes it particularly useful for working the stylet around tight corners without damage to the lead. In some applications, it is particularly desirable to use the flexible tip stylet during insertion, since the flexibility of the stylet makes the lead less likely to perforate the ventricle, or to inhibit working the lead around corners.

As indicated in co-pending application Ser. No. 839,062, there is also provided in chamber 34 at the distal end of lead 10, a member 54 which takes the form of a piston having a generally circular cross section and has a proximal end at which is located a slotted head 58 and a distal end portion 60 which is somewhat smaller in cross sectional diameter than head 58. Head 58 has a slot 61 in the proximal end thereof and is adapted to receive the distal end of stylet 20 which terminates at its distal end in a screwdriver tip 62. When flexible tipped stylet 20 is fully inserted into lead 10 through pin 18, its screwdriver tip portion 62 is firmly seated in slot 61.

An insertion tool 21, is shown in FIG. 1 mounted on pin 18 connected to the proximal end portion of lead 10. The insertion tool 21 is disclosed in a co-pending application entitled Body Implantable Lead With Stylet Rotation Control Device, filed on the same date as the present application.

Rotation of knob 74 and shaft 72 directly transmits rotational torque to stylet 20. The screwdriver blade tip 62 of stylet 20 engages slot 61 in piston 54 and in turn rotates the pointed tip 48 of the helix 42 of the lead to advance it into the body tissue against which the distal tip of the lead was positioned when the rotation of helix 42 was commenced.

Lead 10 may be positioned in the appropriate position in the heart either by using a conventional stylet which is then removed or using the flexible stylet 20 disclosed herein. After the lead is positioned, the screwdriver tip 62 of stylet engages slot 61 of piston 54. The shaft 72 of the insertion tool 21 is then inserted into guide chamber 73 of guide 76 and guide 76 is fitted over pin 18 and the proximal end of lead 10. Handle 74 is then rotated in the correct direction to cause helix 42 to advance it into the tissue against which the distal end of lead 10 was placed.

Although a unipolar lead design has been illustrated in the description of the preferred embodiment, it will be understood that bipolar leads (that is a lead carrying two electrodes and conductors) may as readily utilize the novel structure of the present invention. It should be understood that although the use of the lead 10 has been described for use in a cardiac pacing system, lead 10 could as well be applied to other types of body stimulating systems.

It should be further understood, of course, that the foregoing disclosure relates only to the best mode known to the inventors of many possible modes of practicing the invention and that numerous modifications may be made therein without departing from the spirit and scope of the invention as set forth in the appended claims.

We claim:

1. A stylet for insertion into the proximal opening in the lumen of a hollow vessel to manipulate rotatable means attached to the distal end of said lead, said stylet comprising:

means for manipulating said rotatable means attached to the distal end of said stylet;

a cylindrical body portion, said cylindrical body portion having a first diameter D1 from the proximal end of said stylet to a first point near the distal end of said stylet, said cylindrical body portion having a diameter gradually tapering to a second lesser diameter D2 between said first point and a second point and having said lesser diameter D2 between said second point and a third point, the diameter of said stylet gradually increasing to a larger diameter; and means for rotating said stylet attached to the proximal end of said stylet.

2. The invention of claim 1 wherein the total length of said lesser diameter segment between said second point and said third point is short relative to the length of said stylet.

3. The invention of claim 2 wherein the total length of said lesser diameter segment is approximately 2½ inches.

4. The invention of claim 2 wherein said lesser diameter segment is located in the vicinity of the distal end of said stylet.

5. The invention of claim 4 wherein the total length of said stylet is slightly over 26 inches and the lesser diameter portion begins typically 4½ inches from the distal end of said stylet.

6. The invention of claim 5 wherein the diameter D1 of said stylet is approximately 0.016 inches and the diameter D2 of said lesser diameter segment is 0.013 inches.

7. The invention of claim 6 wherein the transition from the normal diameter of the stylet to the reduced diameter portion between said first point and said second point occurs in the range of ¾ inches of stylet length.

8. The invention of claim 7 wherein the distal end of said stylet is formed into a screwdriver tip having a width of 0.016 inches and a thickness of 0.008 inches.

9. The invention of claim 8 wherein the length of said screwdriver tip is 0.15 inches.

10. The invention of claim 9 wherein said screwdriver tip at the distal end of said stylet has a blade portion which is rounded across its width to a 0.008 inch radius.

11. The invention of claim 10 wherein the transition between the screwdriver tip portion and said stylet occurs over 0.03 inches of stylet length.

* * * * *